(12) United States Patent
Delplanche et al.

(10) Patent No.: US 6,743,373 B1
(45) Date of Patent: Jun. 1, 2004

(54) PROCESS FOR THE SEPARATION OF ENANTIOMERS AND ENANTIOPURE REAGENT

(75) Inventors: Thierry Delplanche, Louvain-la-Neuve (BE); Roland Callens, Grimbergen (BE)

(73) Assignee: Solvay (Societe Anonyme) (BE)

( * ) Notice: Subject to any disclaimer, the term of this patent is extended or adjusted under 35 U.S.C. 154(b) by 0 days.

(21) Appl. No.: 09/549,928

(22) Filed: Apr. 14, 2000

(30) Foreign Application Priority Data

Apr. 21, 1999 (BE) .......................................... 09900280

(51) Int. Cl.$^7$ ................................................. C09K 3/00
(52) U.S. Cl. .................. 252/182.11; 562/434; 562/435; 562/452; 562/453; 562/457
(58) Field of Search ..................... 252/182.11; 562/434, 562/425, 452, 453, 457

(56) References Cited

U.S. PATENT DOCUMENTS

| | | | | |
|---|---|---|---|---|
| 4,885,292 A | * | 12/1989 | Ryono et al. ................ | 514/211 |
| 5,217,958 A | * | 6/1993 | Patel ............................ | 514/19 |
| 5,461,067 A | * | 10/1995 | Norbeck et al. ............. | 514/333 |
| 5,484,801 A | * | 1/1996 | Al-Razzak et al. ......... | 514/365 |
| 5,919,846 A | * | 7/1999 | Batlaw et al. ............... | 524/83 |
| 5,932,758 A | * | 8/1999 | Stingl et al. ................. | 560/39 |

FOREIGN PATENT DOCUMENTS

| | | | |
|---|---|---|---|
| EP | 1046627 A2 | * | 10/2000 |
| GB | 2 127 020 A | | 4/1984 |
| JP | 196765 | * | 2/1990 |
| JP | 69624 | * | 4/1992 |

OTHER PUBLICATIONS

Jürgen Maibaum, "Indirect High–Performance Liquid Chromatographic Resolution of Racemic Tertiary Amines As Their Diastereomeric Urea Derivatives After N–Dealkylation", Journal of Chromatography, 438, pp. 269–278 (1988).
C.J. Gray et al., "Preparation and Properties of Some α–Aza–Amino–Acid Derivatives, Their Possible Use In Peptide Synthesis", Tetrahedron, vol. 33, pp. 739–743 (1977).
C.J. Gray et al., "Synthesis and Spectroscopic Properties of Azaglutamine Amino Acid and Peptide Derivatives", Synthesis, pp. 141–146 (1991).
Peter Marfey, "Determination of D–Amino Acids. II. Use of a Biofunctional Reagent, 1,5–difluoro–2,4–dimitrobenzene", Dep. Chem., Carlsberg Lab., Abstract (1984).
K. Iwaki et al., "Activated Carbamate Reagent as Chiral Derivatizing Agent for Liquid Chromatographic Optical Resolution of Enantiomeric Amino Compounds", Chromatographia, vol. 23, No. 12, pp. 899–902 (1987).
Rompp Chemie–Lexikon, 9$^{th}$ Ed., p. 1860–1861.
Peter Marfey, "Determination of D–Amino Acids. II. Use of a Bifunctional Reagent, 1,5–Difluoro–2,4–Dinitrobenzene", Carlsberg Res. Commun. vol. 49, pp. 591–596 (1984).
Ernest L. Eliel et al., "Stereochemistry of Organic Compounds", pp. 344–381.
Jerry March, "Reactions, Mechanisms and Structure", Advanced organic Chemistry, Fourth Edition, pp. 16–19.

* cited by examiner

Primary Examiner—Cephia D. Toomer
(74) Attorney, Agent, or Firm—Connolly Bove Lodge & Hutz LLP

(57) ABSTRACT

Process for the separation of enantiomers comprising at least one free functional group, in which process a reagent based on an enantiopure amino acid is reacted in basic medium with a mixture comprising enantiometers.

24 Claims, No Drawings

PROCESS FOR THE SEPARATION OF ENANTIOMERS AND ENANTIOPURE REAGENT

The invention relates to a process for the separation of enantiomers and to reagents based on an enantiopure amino acid which can be used in the separation of enantiomers.

The separation of enantiomers is a matter of great importance in the pharmaceutical, chemical and biotechnology industries. This is because the two enantiomers of a chemical substance with an identical composition can have radically different biological activities. It is thus desirable to have available separation reagents and techniques which make it possible to separate the enantiomers and to analyse the enantiomeric purity of pharmaceutical, chemical and biotechnology products.

An article by Marfey, P., (Carlsberg Res. Comm., 49, 1984, 591–596) describes a process for the separation of enantiomers by RP-HPLC. According to this known process, 1-fluoro-2,4-dinitrophenyl-5-L-alaninamide is used as reagent for the derivatization of amino acids. Other similar processes are also known. However, the process and reagent which are described by Marfey and the other processes and reagents exhibit numerous disadvantages.

The derivative obtained in the reaction of the amino acid with the reagent has to be isolated by successive neutralization, drying, redissolution and filtration operations. These operations take a great deal of time and are therefore not very advantageous in an industrial application. Furthermore, there is a risk, in cases of analytical applications, of errors in the analytical results caused by differing solubility of the diastereomeric derivatives in the redissolution solvent. When quantitative analyses are carried out using UV spectrometry, difficulties due to differences in absorption coefficient of the diastereomeric derivatives are encountered in the known process. Finally, the high cost of the reagent renders it desirable to find alternatives.

The invention is targeted at overcoming these problems.

The invention consequently relates to a process for the separation of enantiomers comprising at least one free functional group, in which
 (a) a mixture comprising the enantiomers is reacted in basic medium with a reagent based on an enantiopure amino acid, in which reagent at least one amino group of the amino acid carries an activating group, in order to form an active precursor of an isocyanate group, and in which reagent at least one carboxyl group of the amino acid is substituted, and
 (b) the mixture of diastereomers obtained is subjected to a separation operation.

It has been found, surprisingly, that the process according to the invention makes it possible to obtain good results with regard to the separation of enantiomers comprising at least one free functional group, in particular in quantitative analytical applications. The process according to the invention makes possible rapid derivatization and rapid separation of enantiomers under flexible and economical conditions.

The invention also relates to a reagent based on an enantiopure amino acid in which at least one amino group of the amino acid carries an activating group in order to form an active precursor of an, isocyanate group and in which at least one carboxyl group of the amino acid is substituted.

The term "amino acid" is understood to denote, for the purposes of the present invention, any compound comprising at least one $NH_2$ group and at least one carboxyl group. The amino acids used in the present invention are chiral amino acids comprising at least one asymmetric carbon. Use may be made of any chiral amino acid well known in itself of natural or synthetic origin.

Examples of reagents according to the invention are based, for example, on the following natural amino acids: alanine, valine, norvaline, leucine, norleucine, isoleucine, serine, isoserine, homoserine, threonine, allothreonine, methionine, ethionine, glutamic acid, aspartic acid, asparagine, cysteine, cystine, phenylalanine, tyrosine, tryptophan, lysine, arginine, histidine, ornithine, glutamine and citrulline.

Unnatural enantiomers can also be used.

Examples of amino acids of synthetic origin which can bemused as basis for the reagent according to the invention comprise, for example, the following amino acids: (1-naphthyl)alanine, (2-naphthyl)alanine, homophenylalanine, (4-chlorophenyl)alanine, (4-fluorophenyl)alanine, (3-pyridyl)alanine, phenylglycine, diaminopimelic acid (2,6-diaminoheptane-1,7-dioic acid), 2-aminobutyric acid, 2-aminotetralin-2-carboxylic acid, erythro-β-methylphenylalanine, threo-β-methylphenylalanine, (2-methoxyphenyl)alanine, 1-amino-5-hydroxyindan-2-carboxylic acid, 2-amino-heptane-1,7-dioic acid, (2,6-dimethyl-4-hydroxyphenyl)-alanine, erythro-β-methyltyrosine or threo-β-methyl-tyrosine.

The term "enantiopure amino acid" is understood to denote a chiral amino acid composed essentially of one enantiomer. The enantiomeric excess (ee) is defined: ee $(\%) = 100(x_1-x_2)/(x_1+x_2)$ with $x_1 > x_2$; $x_1$ and $x_2$ represent the content of enantiomer 1 or 2 respectively in the mixture.

Use is generally made of an enantiopure amino acid with an enantiomeric excess of greater than or equal to 99%. Preference is given to an enantiopure amino acid with an enantiomeric excess of greater than or equal to 99.5%. In a particularly preferred way, use is made of an enantiopure amino acid with an enantiomeric excess of greater than or equal to 99.9%.

Any enantiopure amino acid can be used as basis for the reagent according to the invention. The enantiopure amino acid is preferably selected from the abovenamed amino acids of natural or synthetic origin. Amino acids comprising at least one aromatic nucleus, such as, for example, phenylalanine or its derivatives, are particularly well suited as enantiopure amino acid. In a particularly preferred way, the enantiopure amino acid is selected from phenylalanine, (1-naphthyl)-alanine, (2-naphthyl)alanine or α- or β-tryptophan ((2-indolyl)alanine or (3-indolyl)alanine), which are optionally substituted.

In the reagent according to the invention, at least one amino group of the enantiopure amino acid carries an activating group in order to form an active precursor of an isocyanate group.

The term "active precursor of an isocyanate group" is understood to denote any precursor which, when it is employed in a solvent which can be used in the process according to the invention with 1 equivalent of phenylalanine in the presence of 1 equivalent of base, reacts at a temperature of less than or equal to 35° C. essentially completely in a period of time of less than or equal to 30 min to form the corresponding urea. The reactive precursor preferably releases the isocyanate group at a temperature of less than or equal to 30° C. in a period of time of less than or equal to 15 min. In a very particular preferred way, the reactive precursor releases the isocyanate group at room temperature in a period of time of less than or equal to 10 min. Test conditions which can be used to determine the active precursor are described, for example, in Example 3 below.

The activating group is generally composed of a carbonyl derivative bonded to ant electronegative substituent. Use may: be made, for example, as activating group, of an aryloxycarbonyl, heteroaryloxycarbonyl, 1,3-imidazolyl-N-carbonyl or 1,2,4-triazolyl-N-carbonyl group. The aryloxycarbonyl groups which are well suited include those which carry at least one −I, −M substituent on an aromatic nucleus. An −I, −M substituent is a group which has a negative inductive effect and negative resonance effect as defined in J. March, Advanced Organic Chemistry, 4th Ed., 1992, p. 17–19, 273–275. The −I, −M substituents include, for example, $-NO_2$, $-SO_2R$, $-SO_2OR$, $-NR_3^+$ and $SR_2^+$. The substituents are preferably found at at least one of the 2, 4 or 6 positions of the aromatic nucleus or at positions analogous to the 2 or 4 positions in condensed aromatic systems. It is preferable to use an aryloxycarbonyl activating group which carries at least one nitro substituent on the aromatic nucleus. The (4-nitrophenyloxy)carbonyl group is particularly preferred.

In an alternative form, the electronegative substituent comprises an −I substituent (negative inductive effect) independently of the resonance effect (M) as they have been defined above. In this alternative form, the activating group is preferably an aryloxycarbonyl group carrying at least one −I substituent. The −I substituent is preferably found at the positions which were taught above for the −I, −M substituents. Examples of −I substituents which can be used in the reagent according to the invention are, for example, halogens. Chlorine and fluorine are well suited. Fluorine is preferred.

In an alternative form of the invention, everything else being equal, the reagent is based on an enantiopure amino acid in which at least one amino group of the amino acid carries an activating group in order to form an active precursor of an isothiocyanate group. Use may be made, for example, as activating group, of a thiocarbonyl group bonded to an electronegative group as described above. A (4-nitro-phenyloxy)thiocarbonyl or (4-fluorophenyloxy) thio-carbonyl group is preferred.

It has been found that, in this alternative form of the invention, the reaction of the reagent with the organic compound comprising a free functional group generally gives rise to the formation of derivatives comprising a thiocarbonyl group which can give a separation of enantiomers which is further improved with respect to the oxygen-comprising derivatives. The presence of sulphur in the diastereomeric derivatives further facilitates the detection of the said derivatives, in particular by UV spectrometry.

In the reagent according to the invention, at least one carboxyl group of the amino acid is substituted.

The substituent by which the carboxyl group of the amino acid is substituted generally does not comprise a free functional group capable of reacting with the active precursor. The substituents which can be used include, for example, linear or branched alkyl groups comprising from 1 to 4 carbon atoms, such as the methyl, ethyl, n-propyl, isopropyl, n-butyl, isobutyl or t-butyl group, ethers or aryl groups, the alkyl, ethyl or aryl groups optionally being functionalized by, for example, halogens, carboxylic or sulphonic esters, sulphate esters, phosphonic esters or phosphate esters. Hydrophilic, substituents which ensure good solubility of the reagent in mixtures of water with organic solvents are well suited.

The hydrophilic substituent generally ensures that a solution of the reagent in a 1:1 by volume dioxane/water mixture is homogeneous at 20° C. when the concentration of the reagent is at least $0.5 \times 10^{-3}$ mol/l. The concentration is often at least $1 \times 10^{-3}$ mol/l. The concentration is preferably at least $0.5 \times 10^{-2}$ mol/l. Good hydrophilic substituents ensure that the solution is homogeneous at 20° C. when the concentration of the reagent is at least $1 \times 10^{-2}$ mol/l.

It is preferable to employ a substituent which comprises at least one ether bond. Examples of substituents comprising at least one ether bond are, for example, alkyl or aryl ethers of mono-, oligo- or polyalkylene glycols, such as, for example, mono-, oligo- or polyethylene glycol or mono-, oligo- or polypropylene glycol. The 2-methoxyethyl substituent is particularly preferred.

Particularly preferred alternative forms of the reagent according to the invention comprising a hydrophilic substituent correspond to the general formula (I)

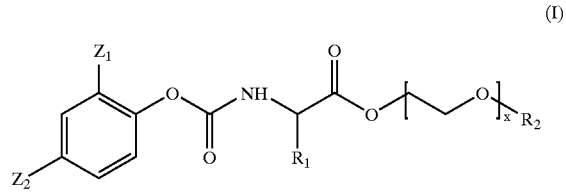

(I)

in which $Z_1$ and/or $Z_2$=$NO_2$, $R_1$=phenyl, α- or β-indolyl, 1-naphthyl or 2-naphthyl, $R_2$=Me, Et, $C_3$–$C_6$ alkyl or $C_3$–$C_6$ cycloalkyl, and x represents an integer from 1 to 5.

In an alternative form, the substituent by which the carboxyl group or the amino acid is substituted comprises at least one chromophore. The term "chromophore" is understood to denote a functional group which absorbs electromagnetic radiation. The absorption maximum of the chromophores is generally from 170 to 2500 nm. The absorption maximum of the chromophores is preferably from 200 to 1000 nm. Examples of chromophores which can be used are aromatic systems optionally substituted in the 2 or 4 position by an −I, −M substituent as described above. The 4-nitrobenzyl, (2-anthraquinonyl)methyl and (9-(9H-fluorenylmethyl)) groups are particularly preferred among the substituents comprising at least one chromophore.

Preferred alternative forms of the reagent according to the invention comprising at least one chromophore correspond to the general formula (II)

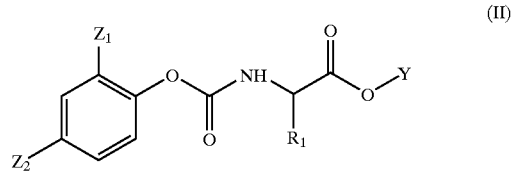

(II)

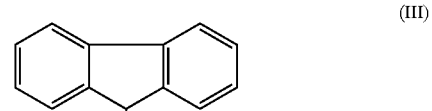

(III)

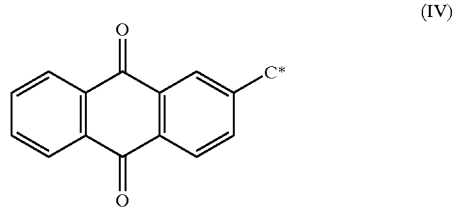

(IV)

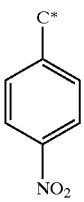

(V)

in which $Z_1$ and/or $Z_2=NO_2$, $R_1$=phenyl, α- or β-indolyl, 1-naphthyl or 2-naphthyl land Y corresponds to any one of the formulae (III to V), the carbon by which Y is bonded to the oxygen of the carboxyl group of the enantiopure amino acid being marked by *.

Use may be made of a hydrophilic substituent comprising at least one chromophore.

Particularly preferred alternative forms of the reagent according to the invention comprising an active precursor of an isothiocyanate group and a hydrophilic substituent correspond to the general formula (VI)

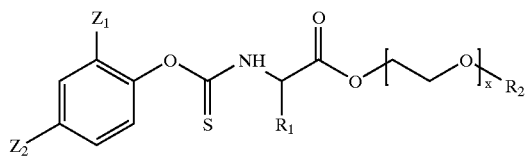

(VI)

in which $Z_1$ and/or $Z_2=NO_2$ or F, $R_1$=phenyl, α- or β-indolyl, 1-naphthyl or 2-naphthyl, $R_2$=Me, Et, $C_3$–$C_6$ alkyl or $C_3$–$C_6$ cycloalkyl and x represents an integer from 1 to 5.

Preferred alternative forms of the reagent according to the invention comprising an active precursor of an isothiocyanate group and at least one chromophore correspond to the general: formula (VII)

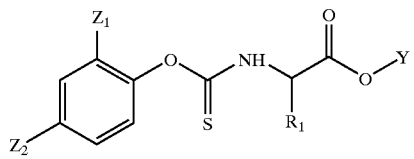

(VII)

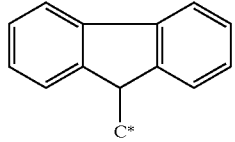

(III)

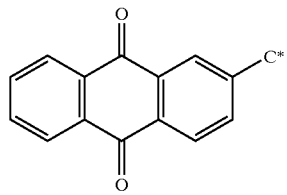

(IV)

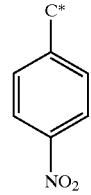

(V)

in which $Z_1$ and/or $Z_2=NO_2$, $R_1$=phenyl, α- or β-indolyl, 1-naphthyl or 2-naphthyl and Y corresponds to any one of the formulae (III to V), the carbon by which Y is bonded to the oxygen of the carboxyl group of the enantiopure amino acid being marked by *.

When the enantiopure amino acid comprises more than one carboxyl group, it is preferable to protect all the carboxyl groups. In a particularly preferred way, all the carboxyl groups are substituted by a substituent as described above.

When free functional groups are present in the enantiopure amino acid, it is preferable to protect the said groups by techniques known in themselves.

The reagent according to the invention can be obtained from the respective enantiopure amino acid. Known methods can be used to carry out the esterification of at least one carboxyl group of the amino acid. It is possible, for example, to employ the enantiopure amino acid and the alcohol corresponding to the substituent to be introduced in an organic solvent, such as, for example, toluene or benzene, in the presence of p-toluenesulphonic acid, preferably under azeotropic esterification conditions. Amino acid ester ammonium tosylate derivatives which are well suited to the introduction of an activating group in order to form an active precursor of an isocyanate group are obtained by this synthetic route.

Mention is made, as example of the introduction of an activating group, of the reaction of an arylox ycarbonyl chloride with the —$NH_2$ group, optionally converted to the ammonium derivative, of an amino acid or of an amino acid ester in basic or neutral medium in a polar organic solvent. Tertiary amine bases, such as, for example, triethylamine or pyridine, are suitable in particular as base. When the operation is carried out in neutral medium, it is preferable to employ sodium hydrogencarbonate. Thus, good results are obtained when an amino acid ester ammonium tosylate is reacted with p-nitrophenyloxycarbonyl chloride in the presence of sodium hydrogencarbonate in a polar organic solvent, such as acetonitrile.

In the process according to the invention, the reagent according to the, invention is reacted in basic medium with a mixture comprising at least enantiomers comprising at least one free functional group.

The reaction of a reagent according to the invention, obtained from the 2-methoxyethyl ester of L-phenylalanine and from 4-nitrophenyl chloroformate, with an amino acid is illustrated in a non-limiting way in Scheme 1 below. The products of this reaction are ureas comprising two amino acids, in which at least one carboxyl functional group is substituted with a substituent.

Scheme 1

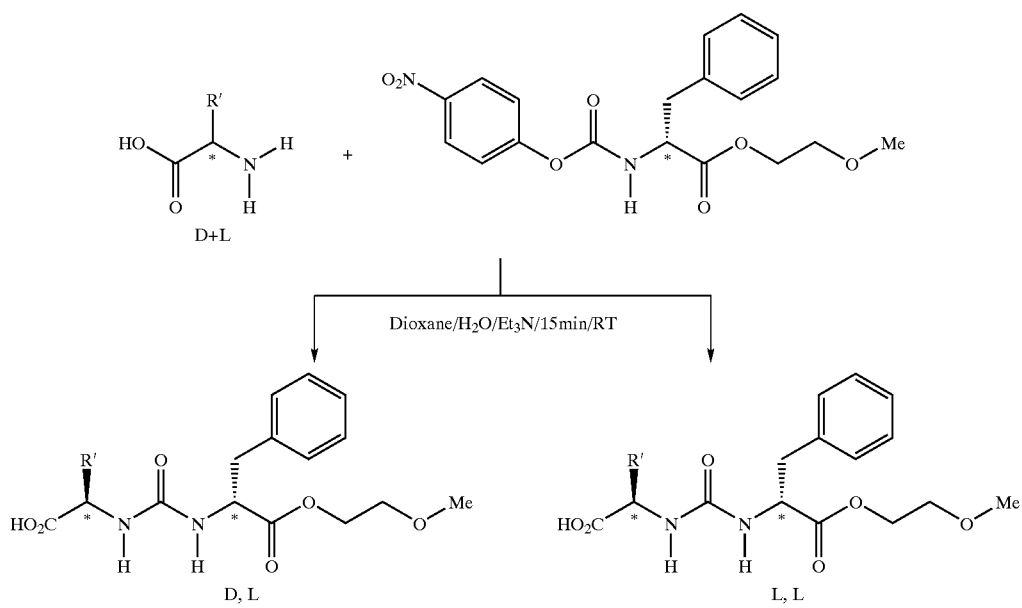

Generally, the free functional group is an optionally monoalkylated amino group, a hydroxyl group or a thiol group. The free functional group can also be composed of an anion, such as, for example, a carbanion or an enolate. The enantiomers comprising at least one free functional group which can be separated by the process according to the invention are generally amino acids, primary or secondary amines, peptides, alcohols, hydroxy acids or thiols. The process according to the invention gives good results in separating the enantiomers of amino acids, such as, for example, the amino acids of natural or synthetic origin mentioned above.

The process according to the invention also gives good results in separating a mixture of enantiomers of imino acids. The term "imino acid" is understood to denote any compound comprising at least one NHR group, in which R represents an organic radical, such as, for example, an alkyl or aryl radical, and at least one carboxyl group. Such imino acids are, for example, those belonging to the group composed of proline, pipecolic acid (piperidine-2-carboxylic acid), morpholine-3-carboxylic acid, piperazine-2-carboxylic acid, 1-thia-4-azacyclohexane-3-carboxylic acid, α-methylproline, cis-4-hydroxy-proline, baikaine (1,2,3,5-tetrahydropyridine-2-carboxylic acid), cis-4-hydroxypipecolic acid, trans-5-hydroxypipecolic acid, 1,2,3,4-tetrahydronorharman-1-carboxylic acid, 1,2,3,4-tetrahydro-6-hydroxy-isoquinoline-3-carboxylic acid, 1,2,3,4-tetrahydro-isoquinoline-3-carboxylic acid, 1,2,3,4-tetrahydro-isoquinoline-1-carboxylic acid and N-methylvaline.

The process according to the invention is carried out in a solvent system in which the mixture of enantiomers and the reagent possess sufficient solubility and the free functional group possesses sufficient nucleophilicity to react with an isocyanate. Systems comprising at least one polar organic solvent and optionally water are suitable, for example, as solvent system. Polar organic solvents which can be used are, for example, aliphatic or alicyclic ethers, such as diethyl ether, tetrahydrofuran or 1,4-dioxane, as well as aliphatic esters, such as, for example, ethyl acetate, aliphatic secondary amides, such as, for example, dimethylformamide and dimethylacetamide or, for example, N-methylpyrrolidone, or acetonitrile.

Good results for organic compounds comprising a free functional group, such as an optionally monoalkylated amino group, an arylichydroxyl group or a thiol group, are obtained in a solvent system comprising a polar organic solvent and water. Dioxane is preferred as polar organic solvent. The ratio by weight of the polar organic solvent to the water in the solvent system is generally less than or equal to 99:1. The ratio is most often less than or equal to 75:25. The ratio is generally greater than or equal to 1:99. The ratio is most often greater than or equal to 25:75.

The invention also relates to a solution of the reagent according to the invention in a polar organic solvent, such as, for example, the polar organic solvents described above. The concentration of the reagent in the solution is generally at least $1 \times 10^{-3}$ mol/l. The concentration is preferably at least $1 \times 10^{-2}$ mol/l. The concentration of the reagent in the solution is generally at most $1 \times 10^{-1}$ mol/l. The concentration is preferably at most $6 \times 10^{-2}$ mol/l. In the solution according to the invention, it is preferable to use a polar organic solvent of analytical purity. If desirable, the solution according to the invention can comprise additives, such as, for example, stabilizers.

The invention also relates to the use of the solution according to the invention in an automatic device for the derivatization and separation of enantiomers of organic compounds comprising at least one free functional group. The amount of the reagent to be employed depends on the number of free functional groups in the organic compound. At least 1 molar equivalent of reagent is employed per free functional group. Generally, at most 10 molar equivalents of reagent are employed per free functional group. Most often, at least 5 molar equivalents of reagent are employed per free functional group. Preferably, at most 3 molar equivalents of reagent are employed per free functional group. In a particularly preferred way, from 1.1 to 2.5 molar equivalents of reagent are employed per free functional group.

The basic nature of the reaction mixture is generated by known methods. The operation is preferably carried out in the presence of at least one base. Tertiary amine bases, such as, for example, triethylamine or diisopropylethylamine, which comprise one basic functionality respectively, or N,N,N',N'-tetramethylethylenediamine, which comprises 2 basic functionalities, are suitable in particular as base.

The amount of base to be employed depends on the amount of the reagent and on the number of basic functionalities in the base. The molar ratio of the reagent to the basic functionalities is generally at least 1. The ratio is generally at most 2. A ratio of 1 gives good results.

In the process according to the invention, the period of time during which the reagent is reacted with the mixture comprising the enantiomers is generally less than or equal to 30 min. Most often, the period of time is less than or equal to 20 min. Preferably, the period of time is less than or equal to 15 min. Good results are obtained with a period of time of greater than or equal to 15 seconds. In practice, a period of time of greater than or equal to 1 min is most often applied. A period of time of 5 to 15 min is highly suitable.

The temperature at which the reagent is reacted with the mixture comprising at least the enantiomers of an organic compound is generally has than or equal to 35° C. The temperature is most often less than or equal to 30° C. The temperature is generally greater than or equal to –20° C. The temperature is most often greater than or equal to 0° C. In a particularly preferred way, the temperature is room temperature, that is to say generally from 15 to 30° C., preferably 20 to 25° C.

In the process according to the invention, the mixture of diastereomers obtained is subjected to a separation operation. The separation operations which can be used for the separation of a mixture of diastereomers are described, for example, in E. Eliel, Stereochemistry of Organic Compounds, 1994, p. 344–381. Mention may be made, as examples, of distillation, crystallization and gas or liquid chromatography operations. Among these operations, liquid chromatography operations, such as, for example, HPLC chromatography, are preferred. In a particularly preferred way, the separation operation is RP-HPLC (reverse phase) chromatography. Information regarding HPLC chromatography is found, for example, in Rompp Chemie-Lexikon, 9th Ed., p. 1860–1861. Use may also be made of thin layer chromatography.

Eluents which can be used in a chromatography operation are known. In the case where the process according to the invention comprises RP-HPLC chromatography as separation operation, good results have been obtained with an eluent comprising acetonitrile or methanol.

In an alternative form of the process according to the invention, which is preferred, the mixture of diastereomers obtained is subjected to the separation operation without prior purification. In known methods for the separation of enantiomers, a crude mixture of diastereomers is isolated, which mixture has to be subjected to purification prior to the separation of the diastereomers. The process and the reagent according to the invention make it possible not to isolate the crude mixture of diastereomers and to carry out the separation operation without prior purification.

The process and the reagent according to the invention can be used for the preparative or analytical separation of enantiomers. The process and the reagents are well suited to the analytical separation of enantiomers. In an alternative form, the process and the reagent are used to determine the enantiomeric excess of an amino acid or of a primary or secondary amine. In another alternative form, the process and the reagent are used to determine the enantiomeric excess of a peptide.

The invention also relates to a process for the production of an enantiopure compound comprising at least one free functional group in which:

(a) a mixture comprising the enantiomers of the compound comprising at least one free functional group is subjected to the separation process according to the invention (b) a cleavage operation is carried out on a pure diastereomer obtained by separation of the mixture of diastereomers (c) the enantiopure compound is recovered.

Use may be made, as cleavage operation, of, for example, an operation of hydrazinolysis in a solvent, such as, for example, an alcohol.

When the process and the reagent according to the invention are used for the analytical separation of enantiomers, use is made of a detection technique known in itself for the determination of the content of enantiomers in the mixture. Optical techniques, such as, for example, UV spectrometry, visible spectrometry or fluorimetry are highly suitable as detection technique.

The examples below are intended to illustrate the invention without, however, limiting it.

EXAMPLE 1

Synthesis of the Reagent According to the Invention

Stage A 1 equivalent of enantiopure amino acid, 1.5 equivalents of para-toluenesulphonic acid monohydrate, 50 equivalents of toluene PA and 5 equivalents of methoxyethanol were introduced into a single-necked round-bottomed flask. The mixture was heated to reflux and the water was removed by means of a Dean and Stark apparatus. After refluxing for 4 hours, the reaction mixture was cooled to room temperature and diluted with ethyl ether. The diluted reaction mixture was placed in a refrigerator for 16 hours. The white solid obtained was filtered off, washed with ether and dried under vacuum.

Stage B $NaHCO_3$ (2.6 equivalents) were weighed into a single-necked round-bottomed flask and: acetonitrile was introduced under a stream of nitrogen:, ($5 \times 10^{-3}$ mol in 36 ml). The mixture was cooled to 0° C. and 4-nitrophenyl chloroformate (1 equivalent), followed by the ammonium salt of the enantiopure amino acid obtained according to Example 1, Stage A (1 equivalent), was successively introduced. The mixture was vigorously stirred for 1 hour at 0° C. and was subsequently brought back to room temperature for 4 hours. At the end of this time, the mixture was transferred into a separating funnel, was diluted with a 1 molar HCl solution and was extracted three times with ether. The combined organic phases were dried over $MgSO_4$, filtered and concentrated under reduced pressure. The crude product was subjected to an appropriate purification treatment.

EXAMPLE 2

Stages A and B were carried out by employing L-phenylalanine as enantiopure amino acid. The crude product was recrystallized from isopropanol until the desired purity was obtained. The yield of Stage B was 64%. A crystalline solid was obtained which was stable on storage at room temperature.

The reagent thus obtained exhibited the following analytical data:

NMR($^1$H): (dioxane reference at 3.71 ppm; product dissolved in $d_6$-dioxane) 8.40 (2H, d): 2H of the (4-nitrophenyloxy)carbonyl 7.44 (7H, m): 2H of the (4-nitrophenyloxy)carbonyl and 5H of the phenyl 7.31 (1H, d): NH of the carbamate 4.83 (1H, m): CH of the phenylalanine 4.41 (2H, m): $CH_2CO=O$ 3.70 (2H, m): $CH_2OMe$ 3.47 (3H, s): $CH_3O$ 3.27 (2H, AB): benzyl 2H Nuclear magnetic resonance (NMR) was performed, in all cases for which an NMR spectrum is shown, with a Brucker AMX 500 MHz device spectrometer. The chemical shifts are shown in ppm with respect to the resonance of TMS (tetramethylsilane). The following abbreviations are used for the appearance of the resonances: m=multiplet, s=singlet, d=doublet, t=triplet and q=quartet. The number nH indicates the number of protons corresponding to the signal.

Melting point: 71–72° C.

Optical rotation [α]: +42.608 (c=0.86 g/100 ml in dioxane), T°=26° C., λ=589 nm)

Thin layer chromatography (TLC) was performed using Merck® 60F-254 silica gel plates. Retention factor, =0.45 (diethyl ether/petroleum ether eluent: 75/25 mixture by volume).

EXAMPLES 3–48

Derivatization and Separation of Mixtures of Enantiomers

The mixture of enantiomers of an organic compound comprising at least one free functional group according to Examples 3–48 (see Table) (1 equivalent) was weighed accurately in a 10 ml vial and was dissolved in distilled water (concentration $5 \times 10^{-3}$ mol/l) in the presence of triethylamine. The molar ratio of the triethylamine with respect to the reagent was 1. The reagent obtained according to Example 1 in which the enantiopure amino acid was L-phenylalanine was introduced into a second 10 ml vial. The reagent was dissolved in dioxane of analytical purity (concentration $3 \times 10^{-2}$ mol/l). The aqueous solution of the amino acid was transferred via a syringe and with vigorous stirring into the solution of the derivatization reagent. After stirring for 15 minutes at room temperature, 500 µl of the reaction mixture was withdrawn and was diluted with 500 µl of dioxane. This solution was analyzed by reverse-phase HPLC by injection of 10 µl of solution onto a Vydac® column.

The following standard conditions were used for the examples of the separation of mixtures of enantiomers by HPLC.

A Vydac® Reverse Phase C18 CAT 201TP54 column was used.

An acetonitrile/$H_2O$ mixture with an acetonitrile gradient of 1.58%/min in the presence of 0.1% by volume of trifluoroacetic acid was employed for the elution.

Detection was performed by UV spectrometry at 205 and 220 nm.

The mixtures of enantiomers which were employed with the reagent obtained according to Example 1 and the separation results obtained are collated in Table 1 below.

TABLE 1

| Ex. | Mixture of enantiomers | $T_r$ L,L[a] | $T_r$ D,L[b] | α[c] | $R_e$[d] | Amount of reagent[e] (Equivalents) |
|---|---|---|---|---|---|---|
| 3 | Alanine | 15.08 | 16.40 | 1.096 | 6.01 | 2 |
| 4 | Valine | 18.73 | 20.94 | 1.127 | 10.83 | 2 |
| 5 | Norvaline | 19.28 | 21.26 | 1.11 | 9.45 | 2 |
| 6 | Leucine | 21.53 | 23.50 | 1.098 | 8.96 | 2 |
| 7 | Norleucine | 22.06 | 23.96 | 1.091 | 8.78 | 2 |
| 8 | Isoleucine | 21.08 | 23.46 | 1.120 | 11.55 | 2 |
| 9 | Threonine | 14.39 | 15.41 | 1.078 | 4.76 | 2 |
| 10 | Allothreonine | 14.39 | 14.85 | 1.036 | 2.09 | 2 |
| 11 | Methionine | 18.97 | 20.59 | 1.092 | 7.74 | 2 |
| 12 |  |  |  |  |  |  |
| 13 | Glutamic acid | 14.56 | 15.00 | 1.033 | 2.07 | 2 |
| 14 | Aspartic acid | 14.22 | 14.66 | 1.034 | 2.08 | 2 |
| 15 | Cysteine | 26.65 | 27.19 | 1.021 | 2.85 | 5* |
| 16 | Cystine | 25.59 | 26.08 | 1.020 | 2.76 | 4* |
| 17 | Proline | 17.09 | 17.75 | 1.042 | 2.75 | 2 |
| 18 | Phenylalanine | 22.64 | 24.08 | 1.068 | 6.25 | 2 |
| 19 | Tyrosine | 28.82 | 29.24 | 1.015 | 1.99 | 5* |
| 20 | Tryptophan | 22.79 | 24.03 | 1.058 | 6.54 | 2 |
| 21 | Ornithine | 24.44 | 24.92 | 1.021 | 2.26 | 6* |
| 22 | Piperidine-2-carboxylic acid (pipecolic acid) | 19.86 | 20.62 | 1.041 | 3.51 | 2 |
| 23 | Morpholine-3-carboxylic acid | 16.05 | 15.56 | 1.034 | 2.28 | 2 |
| 24 | 1-Thia-4-aza-cyclohexane-3-carboxylic acid | 18.76 | 19.43 | 1.038 | 3.30 | 2 |
| 25 | (2-Naphthyl)-alanine | 27.43 | 28.53 | 1.042 | 5.19 | 2 |
| 26 | Homophenyl-alanine | 24.71 | 26.20 | 1.064 | 7.94 | 2 |
| 27 | (4-Chloro-phenyl)-alanine | 25.91 | 27.02 | 1.053 | 5.58 | 2 |
| 28 | (4-Fluoro-phenyl)-alanine | 23.65 | 25.033 | 1.062 | 6.53 | 2 |
| 29 | (3-Pyridyl)-alanine | 14.32 | 13.57 | 1.061 | 3.20 | 2 |
| 30 | Phenylglycine | 20.98 | 22.69 | 1.087 | 8.24 | 2 |
| 31 | 2-Methyl-proline | 19.29 | 20.55 | 1.07 | 5.76 | 2 |
| 32 | cis-4-Hydroxy-proline | 13.92 | 14.44 | 1.041 | 2.19 | 2 |
| 33 | Baikaine | 19.05 | 20.27 | 1.069 | 6.03 | 2 |
| 34 | cis-4-Hydroxypipe-colic acid | 15.12 | 15.91 | 1.058 | 3.97 | 2 |
| 35 | trans-5-Hydroxypipe-colic acid | 13.76 | 14.36 | 1.049 | 2.70 | 2 |
| 36 | 2-Amino-butyric acid | 16.84 | 18.64 | 1.116 | 8.31 | 2 |
| 37 | 1,2,3,4-Tetrahydro-isoquinoline-3-carboxylic acid | 23.71 | 24.75 | 1.046 | 4.89 | 2 |
| 38 | 1,2,3,4-Tetrahydro-isoquinoline-1-carboxylic acid | 23.66$ | 24.67$ | 1.045 | 4.75 | 2 |
| 39 | erythro-β-Methylphenyl-alanine | 24.03$ | 25.73$ | 1.075 | 8.67 | 2 |
| 40 | threo-β-Methylphenyl-alanine | 23.79$ | 25.56$ | 1.079 | 7.22 | 2 |

TABLE 1-continued

| Ex. | Mixture of enantiomers | $T_r$ L,L[a] | $T_r$ D,L[b] | $\alpha$[c] | $R_e$[d] | Amount of reagent[e] (Equivalents) |
|---|---|---|---|---|---|---|
| 41 | o-Methoxy-phenylalanine | 23.08$ | 24.31$ | 1.057 | 5.64 | 2 |
| 42 | 1,2,3,4-Tetrahydro-norharman-1-carboxylic acid | 26.26$ | 27.09$ | 1.031 | 3.44 | 5* |
| 43 | 1,2,3,4-Tetrahydro-6-hydroxy-isoquinoline-3-carboxylic acid | 29.14$ | 29.67$ | 1.019 | 2.49 | 5* |
| 44 | 2-Amino-heptane-1,7-dioic acid | 18.09$ | 19.21$ | 1.067 | 6.41 | 2 |
| 45 | erythro-β-Methyl-tyrosine | 29.84$ | 30.53$ | 1.024 | 3.65 | 5* |
| 46 | threo-β-Methyl-tyrosine | 29.51$ | 30.07$ | 1.02 | 2.97 | 5* |
| 47 | N-Methyl-valine | 21.47 | 22.59 | 1.056 | 5.62 | 2 |
| 48 | 2-Hydroxy-methyl-piperidine | 19.79 | 20.4 | 1.033 | 2.73 | 2 |

\* Derivatization also of the functional group carried by the side chain.
$ The attribution of the retention times to the (L,L) and (D,L) isomers respectively is uncertain as the mixture of the enantiomers subjected to the separation was racemic.

Key for Tables 1 to 6

(a): Retention time corresponding to the derivative of the L enantiomer (L,L)

(b): Retention time corresponding to the derivative of the D enantiomer (D,L)

(c): Separation factor; $\alpha=(T_r 2-T_r 0)(T_r 1-T_r 0)$, where $T_r 2$ and $T_r 1$ are the retention times of the second and first compounds respectively and $T_r 0$ is the retention time of a non-retained compound.

(d): Peak resolution:

$$R_s = 0.25\left(\frac{\alpha-1}{\alpha}\right)\left(\frac{k'2}{1+k'2}\right)\sqrt{N_2}$$

where k'2 is the capacity factor of the second compound and N is the number of theoretical plates.

EXAMPLE 49

Stages A and B were carried out by employing L-(2-naphthyl)alanine as enantiopure amino acid. The crude product was recrystallized from isopropanol until the desired purity was obtained. The yield of Stage B was 77%. A crystalline solid was obtained which was stable on storage at room temperature.

The following NMR spectrum of the reagent was obtained:

NMR($^1$H): (dioxane reference at 3.71 ppm; product dissolved in $d_6$-dioxane) 8.20 (2H, d): 2H of the (4-nitrophenyloxy)carbonyl 7.79 (4H, m) 4H of the naphthyl 7.45 (3H, d): 3H of the naphthyl 7.21 (3H, m): 2H of the (4-nitrophenyloxy)carbonyl and 1H of the naphthyl 4.78 (1H, m) CH of the naphthylalanine 4.27 (2H, m): $CH_2CO=O$ 3.52 (2H, m): $CH_2OMe$ 3.28 (3H, s): $CH_3O$ 3.29 (2H, AB): benzyl 2H Melting point: 76–77° C.

Optical rotation: [α]: 83.5 (c=1.025 g/100 ml in dioxane, T°=26° C., λ=589 nm)

Thin layer chromatography (TLC) was performed by using Merck® 60F-254 silica gel plates. Former retention factor=0.4 (diethyl ether/petroleum ether eluent: 75/25 mixture by volume).

The reaction of the 2-methoxyethyl ester of L-N-(4-nitrophenoxy)carbonyl-(2-naphthyl)alanine with a mixture of arginine enantiomers and the separation operation was carried out under the conditions of Examples 3–48. 2 equivalents of reagent and 2 equivalents of triethylamine per equivalent of arginine were employed.

The separation result obtained is shown in Table 2 below.

TABLE 2

| Ex. | Mixture of enantiomers | $T_r$ L,L[a] | $T_r$ D,L[b] | $\alpha$[c] | $R_e$[d] | Amount of reagent[e] (Equivalents) |
|---|---|---|---|---|---|---|
| 49 | Arginine | 20.168 | 19.625 | 1.030 | 1.73 | 2 |

EXAMPLE 50

The reaction of the 2-methoxyethyl ester of L-N-(4-nitrophenoxy)carbonyl-β-tryptophan with a mixture of valine enantiomers and the separation operation were carried out under the conditions of Examples 3–48. 2 equivalents of reagent and 2 equivalents of triethylamine per equivalent of valine were employed.

The separation result obtained is shown in Table 3 below.

TABLE 3

| Ex. | Mixture of enantiomers | $T_r$ L,L[a] | $T_r$ D,L[b] | $\alpha$[c] | $R_e$[d] | Amount of reagent[e] (Equivalents) |
|---|---|---|---|---|---|---|
| 50 | Valine | 19.19 | 20.42 | 1.069 | 5.80 | 2 |

EXAMPLE 51

Preparation of the 4-Nitrobenzyl Ester of N-((4-Nitrophenoxy)carbonyl)phenylalanine Stage A:

4 g (1 eq) of Z-(L)-phenylalanine, 2.89 g (1 eq) of 4-nitrobenzyl bromide and 26 ml (25 eq) of dimethylformamide were introduced into a single-necked round-bottomed flask. 1.55 g (2 eq) of dry potassium fluoride were then added under nitrogen. The mixture was stirred at 60° C. for 16 hours. The reaction mixture was cooled to room temperature and diluted with 100 ml of ethyl acetate. The organic phase was washed with two, times 100 ml of a 5% $NaHCO_3$ solution and with two times 100 ml of water. The organic phase was dried over $MgSO_4$, filtered and concentrated under reduced pressure. The solid obtained was dried in an oven overnight.

Yield: 6.3 g (85%)

Stage B:

The solid obtained in Stage 1: was diluted in 25 ml of glacial acetic acid. 6.9 ml (3 eq) of a 33% by weight solution of HBr in acetic acid were carefully added. The mixture was stirred for one and a half hours at room temperature. The mixture was diluted with 200 ml of ethyl ether and the white precipitate formed was filtered off and washed with three times 200 ml of ethyl ether. The solid was dried in an oven overnight.

Yield: 5.53 g (99%)
Stage C:
0.82 g of NaHCO$_3$ (2.6 eq) was weighed in a single-necked round-bottomed flask and 27 ml of acetonitrile (135 eq) were introduced under a stream of nitrogen. The mixture was cooled to 0° C. and 0.81 g (1 eq) of 4-nitrophenyl chloroformate, followed by 1.5 g (1 eq) of the bromine salt of the phenylalanine-4-nitrobenzyl derivative, were successively introduced. The mixture was stirred vigorously for 1 hour at 0° C. and was subsequently brought back to room temperature for 11 hours. At the end of this time, the mixture was transferred into a separating funnel, was diluted with 60 ml of a 1M hydrochloric acid solution and was extracted with three times 60 ml of ethyl acetate. The combined organic phases were dried over MgSO$_4$, filtered and concentrated under reduced pressure to give a beige solid. The latter was triturated in 50 ml of ether and filtered off.

Yield: 1.44 g (82%)

NMR($^1$H): (methanol reference at 3.32 ppm; product dissolved in d$_4$-methanol) 8.32 (2H, d): 2H of the (4-nitrophenyloxy)-carbonyl 8.28 (2H, d): 2H of the 4-nitrobenzoyl 7.63 (2H, d): 2H of the 4-nitrophenyoxycarbonyl 7.34–7.41 (7H, m): 2H of the 4-nitrobenzyl and 5H of the phenyl 5.37 (2H, s): benzyl CH$_2$ of the 4-nitrobenzyl 4.65 (1H, m): CH of the phenylalanine 3.23 (2H, AB): benzyl CH$_2$ of the phenylalanine Melting point: 118.3° C.

Optical rotation: [α]: +20.83 (c=0.96 g/100 ml in dioxane, T°=26° C., λ=589 nm)

Thin layer chromatography (TLC) was performed by using Merck® 60F-254 silica gel plates. Retention factor =0.4 (diethyl ether/petroleum ether eluent: 75/25 mixture by volume).

EXAMPLE 52

The result of the separation of a mixture of valine enantiomers which was carried out with the reagent obtained according to Example 51 according to the procedure of Example 3 is presented in Table 4.

Detection was performed by UV spectrometry at 205, 220 and 270 nm.

procedure of Example 51. The result of the separation of a mixture of valine enantiomers which was carried out with the reagent obtained according to Example 51 according to the procedure of Example 3 is presented in Table 5.

The detection was performed by UV spectrometry at 205, 220, 270 and 330 nm.

TABLE 5

| Ex. | Mixture of enantiomers | T$_r$ L,L$^{(a)}$ | T$_r$ D,L$^{(b)}$ | α$^{(c)}$ | R$_s^{(d)}$ (nm) | Equivalents of reagents | R$_s$ (nm) |
|---|---|---|---|---|---|---|---|
| 52 | Valine | 30.168 | 30.884 | 1.025 | 3.01 (205 nm) | 2 | 3.11 (270 and 330) |

It was observed that this reagent makes possible detection at 270 nm and 330 nm. A slightly greater separation factor was obtained at these wavelengths than when detection was performed at 205 nm.

It is apparent that the reagent according to the invention can be easily obtained. The reagent according to the invention exhibits good stability at room temperature.

The process according to the invention makes it possible to separate a greater variety of chiral organic compounds comprising at least one free functional group in a simple and fast way and under uniform separation conditions without having to isolate the reaction product prior to the separation stage.

EXAMPLE 54

NaHCO$_3$ (2.6 equivalents) was weighed in a single-necked round-bottomed flask and acetonitrile was introduced under a stream of nitrogen (12×10$^{-3}$ mol in 83 ml). The mixture was cooled to 0° C. and 4-fluorophenyl chlorothioformate (1 equivalent), followed by the enantiopure amino acid ammonium salt obtained according to Example 2, Stage A (1 equivalent), were successively introduced. The mixture was stirred vigorously for 1 hour at 0° C. and was subsequently brought back to room temperature for 4 hours. At the end of this time, the mixture was transferred into a separating funnel, was diluted with a 1 molar HCl solution and was extracted three times with ether. The combined organic phases were dried over MgSO$_4$, filtered and concentrated under reduced pressure. The crude product was subjected to an appropriate purification treatment. The reagent thus obtained was (S)-N-(4-fluorophenoxy-

TABLE 4

| Ex. | Mixture of enantiomers | T$_r$ L,L$^{(a)}$ | T$_r$ D,L$^{(b)}$ | α$^{(c)}$ | R$_s^{(d)}$ (nm) | Equivalents of reagents | R$_s$ (nm) |
|---|---|---|---|---|---|---|---|
| 52 | Valine | 26.207 | 27.246 | 1.042 | 3.92 (205 nm) | 2 | 4.77 (220–270) |

It was observed that this reagent makes possible detection at 220 nm and 270 nm. A greater separation factor was obtained at these wavelengths than when detection was carried out at 205 nm.

EXAMPLE 53

The 2-methylanthraquinone ester of N-((4-nitrophenoxy)carbonyl)phenylalanine was synthesized according to the thiocarbonyl)phenylalanine methoxyethyl ester. It exhibited the following analytical data:

NMR ($^1$H): (dioxane ref at 3.71 ppm; product dissolved in d$_6$-dioxane) 8.88 (2H, d): 2H of the 4-fluorophenoxythiocarbonyl 7.20–7.49 (7H, m): 2H of the fluorophenoxythiocarbonyl and 5H of the phenyl 6.99 (1H, d): NH of the carbamate 5.36 (1H, m): CH of the phenylalanine 4.42 (2H, m): CH₂OC↑O 3.69 (2H, m): CH₂OMe 3.48 (3H, s): CH₃O 3.41 (2H, AB): benzyl 2H

EXAMPLES 55–57

The derivatization and separation of the mixtures of enantiomers of organic compounds comprising a free functional group of Examples 55–57 (Table) were carried out under the conditions of Examples 3–48 by using, as reagent, the reagent obtained in Example 54. Detection was performed only at 245 nm. The separation results obtained are shown in the table below.

TABLE 6

| Ex. | Mixture of enantio-mers | $T_r L,L^{(a)}$ | $T_r D,L^{(b)}$ | $\alpha^{(c)}$ | $R_e^{(d)}$ | Amount of reagent (Equivalents) |
| --- | --- | --- | --- | --- | --- | --- |
| 55 | Valine | 24.79 | 22.11 | 1.129 | 12.89 | 2 |
| 56 | Proline | 19.42 | 21.22 | 1.099 | 7.69 | 2 |
| 57 | Tyrosine | 22.14 | 23.26 | 1.054 | 4.4 | 5 |

The reagent makes possible very efficient separation of enantiomers. Detection by UV spectrometry can be performed at a single wavelength and it is highly sensitive.

What is claimed is:

1. A reagent of formula

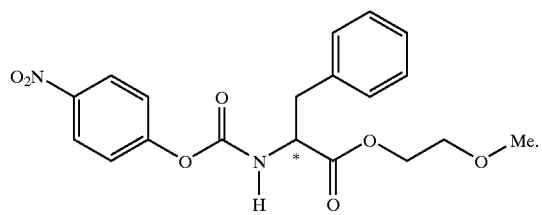

2. A reagent comprising a 2- and/or 4-substituted phenyloxy carbonyl group bonded to at least one amino group of an enantiopure amino acid and said enantiopure amino acid further contains at least one carboxyl group and said enantiopure amino acid is selected from the group consisting of phenylalanine, (1-naphthyl)-alanine, (2-naphthyl)-alanine, (2-indolyl)alanine and (3-indolyl)-alanine;

wherein said substituent at the 2 and/or 4 position of said substituted phenyloxy carbonyl group is selected from the group consisting of groups having a negative inductive effect and groups having a negative resonance effect;

and said carboxyl group in the amino acid is bonded to (a) or (b), wherein
  (a) is a substituent comprising at least one ether bond, and is a substituent comprising a chromophore selected from aromatic systems substituted in the 2 or 4 position by a substituent having a negative inductive effect and a negative resonance effect, (2-anthraquinoyl)methyl, and (9-(9H-fluorenylmethyl)) groups.

3. The reagent according to claim 2, in which at least one amino group of the enantiopure amino acid carries on activating group in order to form an active precursor of an isocyanate group.

4. A reagent corresponding to the general formula (I)

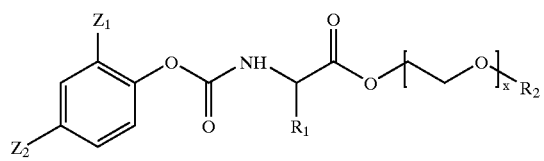

in which $Z_1$ and/or $Z_2$=NO₂, $R_1$=phenyl, α- or β-indolyl, 1-naphthyl or 2-naphthyl, $R_2$=Me, Et, $C_3$–$C_6$ alkyl or $C_3$–$C_6$ cycloalkyl, and x represents an integer from 1 to 5.

5. A reagent comprising at least one chromophore, corresponding to the general formula (II)

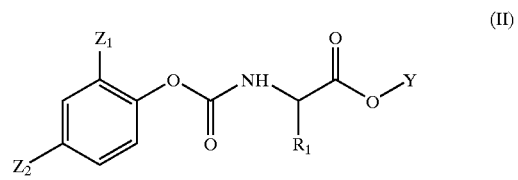

in which $Z_1$ and/or $Z_2$=NO₂, $R_1$=phenyl, α- or β-indolyl, 1-naphthyl or 2-naphthyl and Y corresponds to any one of the formulae (III to V),

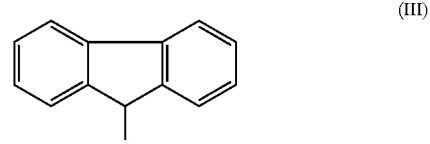

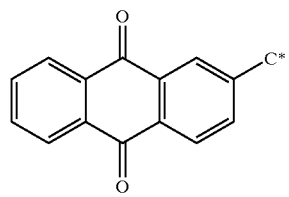

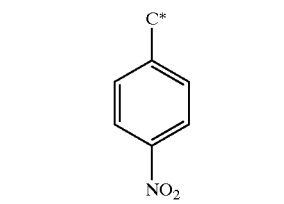

the carbon by which Y is bonded to the oxygen of the carboxyl group of the enantiopure amino acid being marked by *.

6. A reagent corresponding to the general formula (VI)

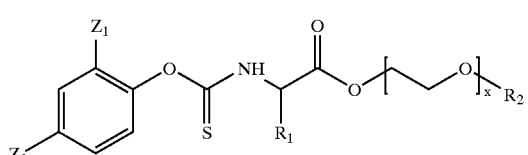

in which $Z_1$ and/or $Z_2$=NO$_2$ or F, $R_1$=phenyl, α- or β-indolyl, 1-naphthyl or 2-naphthyl, $R_2$=Me, Et, $C_3$–$C_6$ alkyl or $C_3$–$C_6$ cycloalkyl, and x represents an integer from 1 to 5.

7. A solution of the reagent according to claim 2 in a polar organic solvent.

8. The reagent of claim 2, wherein the carboxyl group is substituted by at least one substituent selected from the group consisting of a hydrophilic substituent and a substituent comprising at least one chromophore.

9. The reagent of claim 2, comprising 2-methoxyethyl-(N-4-nitrophenyloxycarbonyl)-phenylalanine.

10. The reagent of claim 2, wherein at least one of said substituent at the 2- and/or 4-position of the substituted phenyloxy carbonyl is selected from the group consisting of —NO$_2$, chlorine and fluorine.

11. The reagent of claim 5, wherein Y is selected from the group consisting of alkyl and aryl ethers of mono-, oligo-, or polyalkylene glycols.

12. The reagent of claim 5, wherein Y is 2-methoxyethyl.

13. The reagent of claim 2, wherein at least one of said substituent at the 2- and/or 4-position of the substituted phenyloxy carbonyl is selected from the group consisting of —NO$_2$, —SO$_2$R, —SO$_2$OR, —NR$_3^+$ and SR2$^+$.

14. The reagent of claim 2, wherein at least one of said substituent at the 2- and/or 4-position of the substituted phenyloxy carbonyl is selected from the group consisting of —NO$_2$.

15. The reagent of claim 2, wherein said substituent having a negative inducting effect and a negative resonance effect is selected from the group consisting of —NO$_2$, —SO$_2$R, —SO$_2$OR, —NR$_3^+$ and SR$_2^+$.

16. A reagent comprising a 2- and/or 4-substituted phenyloxy thiocarbonyl group bonded to at least one amino group of an enantiopure amino acid and said enantiopure amino acid further contains at least one carboxyl group and said enantiopure amino acid is selected from the group consisting of alanine, valine, norvaline, leucine, norleucine, isoleucine, serine, isoserine, homoserine, threonine, allothreonine, methionine, ethionine, glutamic acid, aspartic acid, asparagine, cysteine, cystine, phenylalanine, tyrosine, tryptophane, lysine, arginine, histidine, ornithine, glutamine, citrulline, (1-naphthyl)alanine, (2-naphthyl)alanine, homophenylalanine, (4-chlorophenyl)alanine, (4-fluorophenyl)alanine, (3-pyridyl)alanine, phenylglycine, diaminopimelicacid (2,6-diaminoheptaine-1, 7-dioic acid), 2-aminobutyric acid, 2-aninotetraline-2-carboxylic acid, erythro-β-methylphenylalanine, threo-β-methylphenylalanine, (2-methoxyphenyl)alanine, 1-amino-5-hydroxyindan-2-carboxylic acid, 2-aminoheptane-1, 7-dioic acid, (2,6-dimethyl-4-hydroxyphenyl)alanine, erythro-β-methyltyrosine and threo-β-methyltyrosine;

wherein said substituent at the 2 and/or 4 position of said substituted phenyloxy thiocarbonyl group is selected from the group consisting of groups having a negative inductive effect and groups having a negative resonance effect;

and said carboxyl group in the amino acid is bonded to (a) or (b), wherein (a) is a substituent comprising at least one ether bond, and (b) is a substituent comprising a chromophore selected from aromatic systems substituted in the 2 or 4 position by a substituent having a negative inductive effect and a negative resonance effect, (2-anthraquinoyl)methyl, and (9-(9H-fluorenylmethyl)) groups.

17. The reagent of claim 16, wherein at least one of said substituent at the 2- and/or 4-position of the substituted phenyloxy carbonyl is selected from the group consisting of —NO$_2$, chlorine and fluorine.

18. The reagent of claim 16, wherein said enantiopure amino acid is selected from the group consisting of phenylalanine, (1-naphthyl)-alanine, (2-naphthyl)-alanine, (2-indolyl)alanine and (3-indolyl)alanine.

19. The reagent of claim 6, wherein Y is selected from the group consisting of alkyl and aryl ethers of mono-, oligo-, or polyalkylene glycols.

20. The reagent of claim 6, wherein Y is 2-methoxyethyl.

21. The reagent of claim 16, wherein at least one of said substituent at the 2- and/or 4-position of the substituted phenyloxy carbonyl is selected from .the group consisting of —NO$_2$, —SO$_2$R, —SO$_2$OR, —NR$_3^+$ and SR$_2^+$.

22. The reagent of claim 16, wherein at least one of said substituent at the 2- and/or 4-position of the substituted phenyloxy carbonyl is selected from the group consisting of —NO$_2$.

23. The reagent of claim 16, wherein said substituent having a negative inducting effect and a negative resonance effect is selected from the group consisting of —NO$_2$, —SO$_2$R, —SO$_2$OR, —NR$_3^+$ and SR$_2^+$.

24. A reagent comprising a 2- and/or 4-substituted phenyloxy carbonyl group bonded to at least one amino group of an enantiopure amino acid and, said enantiopure amino acid further contains at least one carboxyl group and said enantiopure amino acid is selected from the group consisting of alanine, valine, norvaline, leucine, norleucine, isoleucine, serine, isoserine, homoserine, threonine, allothreonine, methionine, ethionine, glutamnic acid, aspartic acid, asparagine, cysteine, cystine, phenylalanine, tyrosine, tryptophane, lysine, arginine, histidine, ornithine, glutamine, citrulline, (1-naphthyl)alanine, (2-naphthyl)alanine, homophenylalanine, (4-chlorophenyl)alanine, (4-fluorophenyl)alanine, (3-pyridyl)alanine, phenylglycine, diaminopimelicacid (2,6-diaminoheptaine-1,7-dioic acid), 2-aminobutyric acid, 2-aminotetraline-2-carboxylic acid, erythro-β-methylphenylalanine, threo-β-methylphenylalanine, (2-methoxyphenyl)alanine, 1-amino-5-hydroxyindan-2-carboxylic acid, 2-aminoheptane-1, 7-dioic acid, (2,6-dimethyl-4-hydroxyphenyl)alanine, erythro-β-methyltyrosine and threo-β-methyltyrosine;

wherein said substituent at the 2 and/or 4 position of said substituted phenyloxy carbonyl group is selected from the group consisting of groups having a negative inductive effect and groups having a negative resonance effect;

and said carboxyl group in the amino acid is bonded to (a) or (b), wherein (a) is a substituent comprising at least one ether bond, and is a substituent comprising at least one chromophore, correspond to the general formula (VII)

(VII)

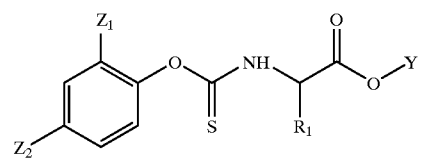

in which $Z_1$ and/or $Z_2$=NO$_2$, $R_1$=phenyl, α- or β-indolyl, 1-naphthyl or 2-naphthyl and Y correspond to any one of the formulae (III to V),
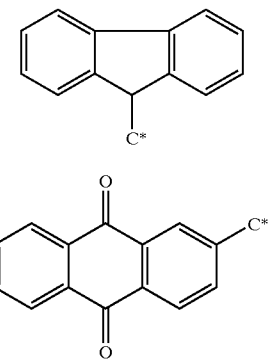
(III)
(IV)
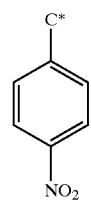
(V)
the carbon by which Y is bonded to the oxygen of the carboxyl group of the enantiopure amino acid being marked by *.
* * * * *

UNITED STATES PATENT AND TRADEMARK OFFICE
CERTIFICATE OF CORRECTION

PATENT NO. : 6,743,373 B1
DATED : June 1, 2004
INVENTOR(S) : Thierry Delplanche et al.

It is certified that error appears in the above-identified patent and that said Letters Patent is hereby corrected as shown below:

Column 20,
Line 32, "glutamnic" should read -- glutamic --.
Line 67, "correspond" should read -- corresponds --.

Signed and Sealed this

Ninth Day of November, 2004

JON W. DUDAS
*Director of the United States Patent and Trademark Office*